US00PP32341P2

(12) United States Plant Patent
van den Haak

(10) Patent No.: US PP32,341 P2
(45) Date of Patent: Oct. 13, 2020

(54) ***HEUCHERA* PLANT NAMED 'IFHERB'**

(50) Latin Name: ***Heuchera* hybrid**
Varietal Denomination: IFHERB

(71) Applicant: Jelle van den Haak, Amsterdam (NL)

(72) Inventor: Jelle van den Haak, Amsterdam (NL)

(73) Assignee: Innoflora Plant Breeding B.V., Heerhugowaard (NL)

( * ) Notice: Subject to any disclaimer, the term of this patent is extended or adjusted under 35 U.S.C. 154(b) by 113 days.

(21) Appl. No.: 16/501,555

(22) Filed: Apr. 29, 2019

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Heuchera* plant named 'IFHERB', characterized by its compact and uniformly mounded plant habit; densely foliated and bushy appearance; dark greyed purple-colored leaves; long flowering period; numerous inflorescences with red purple-colored flowers; and good garden performance.

2 Drawing Sheets

Botanical designation: *Heuchera* hybrid.
Cultivar denomination: 'IFHERB'.

BACKGROUND OF THE INVENTION

The present invention relates to a new and distinct *Heuchera* plant, botanically known as *Heuchera* hybrid and hereinafter referred to by the name 'IFHERB'.

The objective of the breeding program is to create new compact *Heuchera* plants with attractive leaf coloration and good garden performance.

The new *Heuchera* plant originated from a cross-pollination in May, 2011 in Andijk, The Netherlands of a proprietary selection of *Heuchera* hybrid identified as code number 083-11-K013-01, not patented, as the female, or seed, parent with a proprietary selection of *Heuchera* hybrid identified as code number 083-11-K011-03, not patented, as the male, or pollen, parent. The new *Heuchera* plant was discovered and selected by the Inventor as a single flowering plant from within the progeny of the stated cross-pollination in a controlled greenhouse environment in Andijk, The Netherlands in June, 2012.

Asexual reproduction of the new *Heuchera* plant by in vitro meristem culture in a controlled environment in Andijk, The Netherlands since May, 2015 has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'IFHERB'.

These characteristics in combination distinguish 'IFHERB' as a new and distinct *Heuchera* plant:

1. Compact and uniformly mounded plant habit.
2. Densely foliated and bushy appearance.
3. Dark greyed purple-colored leaves.
4. Long flowering period.
5. Numerous inflorescences with red purple-colored flowers.
6. Good garden performance.

Plants of the new *Heuchera* differ primarily from plants of the female parent selection in leaf color as plants of the new *Heuchera* have dark greyed purple-colored leaves whereas plants of the female parent selection have purple and white-colored leaves. In addition, plants of the new *Heuchera* differ from plants of the female parent selection in flower color as plants of the new *Heuchera* have red purple-colored flowers whereas flowers of plants of the female parent selection have pure white-colored flowers.

Plants of the new *Heuchera* differ primarily from plants of the male parent selection in leaf color as plants of the new *Heuchera* have dark greyed purple-colored leaves whereas plants of the male parent selection have red-colored leaves.

Plants of the new *Heuchera* can be compared to plants of *Heuchera* hybrid 'TNHEUFR', disclosed in U.S. Plant Pat. No. 29,644. In side-by-side comparisons, plants of the new *Heuchera* differ primarily from plants of 'TNHEUFR' in the following characteristics:

1. Plants of the new *Heuchera* grow slower than plants of 'TNHEUFR'.
2. Plants of the new *Heuchera* and 'TNHEUFR' differ in leaf color as plants of the new *Heuchera* have dark greyed purple-colored leaves whereas plants of 'TNHEUFR' have red to burgundy-colored leaves.
3. Plants of the new *Heuchera* and 'TNHEUFR' differ in flower color as plants of the new *Heuchera* have red purple-colored flowers whereas plants of 'TNHEUFR' have pure white-colored flowers.

BRIEF DESCRIPTION OF THE PHOTOGRAPHS

The accompanying colored photographs illustrates the overall appearance of the new *Heuchera* plant showing the colors as true as it is reasonably possible to obtain in colored reproductions of this type. Colors in the photographs may differ slightly from the color values cited in the detailed botanical description which accurately describe the colors of the new *Heuchera* plant.

The photograph on the first sheet is a side perspective view of a typical flowering plant of 'IFHERB' grown in a container.

The photograph at the top of the second sheet is a close-up view of typical leaves of 'IFHERB'.

The photograph at the bottom of the second sheet is a close-up view of a typical inflorescence of 'IFHERB'.

DETAILED BOTANICAL DESCRIPTION

The aforementioned photographs and following observations, measurements and values describe plants grown during the summer with three plants in a 15-cm containers in an outdoor nursery in Heerhugowaard, The Netherlands and under cultural practices typical of commercial *Heuchera* production. During the production of the plants, day temperatures ranged from 10° C. to 25° C. and night temperatures ranged from 4° C. to 15° C. Plants were 18 weeks old when the photographs and the description were taken. In the description, color references are made to The Royal Horticultural Society Colour Chart, 2015 Edition, except where general terms of ordinary dictionary significance are used.

Botanical classification: *Heuchera* hybrid 'IFHERB'.

Parentage:

- *Female, or seed, parent*.—Proprietary selection of *Heuchera* hybrid identified as code number 083-11-K013-01, not patented.
- *Male, or pollen, parent*.—Proprietary selection of *Heuchera* hybrid identified as code number 083-11-K011-03, not patented.

Propagation:

- *Type*.—By in vitro meristem culture.
- *Time to initiate roots, summer*.—About ten days at temperatures about 22° C.
- *Time to initiate roots, winter*.—About 15 days at temperatures about 20° C.
- *Time to produce a rooted young plant, summer*.—About 42 days at temperatures about 20° C.
- *Time to produce a rooted young plant, winter*.—About 50 days at temperatures about 20° C.
- *Root description*.—Fine, fibrous; typically light brown in color, actual color of the roots is dependent on substrate composition, water quality, fertilizer type and formulation, substrate temperature and physiological age of roots.
- *Rooting habit*.—Freely branching; medium density.

Plant description:

- *Plant and growth habit*.—Herbaceous perennial; basal rosette plant habit with leaves developing from the base; densely foliated and dense and bushy appearance; compact and uniformly mounded plant habit; moderately vigorous growth habit; moderate growth rate.
- *Plant height, soil level to top of foliar plane*.—About 28 cm.
- *Plant height, soil level to top of inflorescences*.—About 59.6 cm.
- *Plant diameter or spread*.—About 63 cm.

Leaf description:

- *Arrangement*.—Alternate in basal rosettes; simple.
- *Length*.—About 15.2 cm.
- *Width*.—About 14.5 cm.
- *Shape*.—Broadly ovate; palmately lobed.
- *Apex*.—Obtuse with a small and short abruptly acute tip.
- *Base*.—Hastate, lobes touching to slightly imbricate.
- *Margin*.—About seven lobe per leaf; crenate with small and short abruptly acute tips; sinuses medium in depth and divergent; moderately to strongly undulate.
- *Texture and luster, upper surface*.—Sparsely pubescent; slightly glossy.
- *Texture and luster, lower surface*.—Sparsely pubescent; moderately glossy.
- *Venation pattern*.—Palmate; reticulate.
- *Color*.—Developing leaves, upper surface: Close to 185A. Developing leaves, lower surface: Close to 187C. Fully expanded leaves, upper surface: Close to between N77C and N187B to N187C; distally, close to between N87A and 200A; venation, close to between 200A and 203C. Fully expanded leaves, lower surface: Close to between N77A and 187A to 187B; venation, close to N79B to N79C.
- *Petioles*.—Length: About 19.9 cm. Diameter: About 3 mm. Strength: Moderately strong. Texture and luster, upper and lower surfaces: Densely pubescent; moderately glossy. Color, upper surface: Close to N186C. Color, lower surface: Close to 187A.
- *Stipules*.—Quantity and arrangement: One at the base of each leaf. Length: About 1.5 cm. Width: About 4 mm. Shape: Lanceolate with acute apex. Color, upper and lower surfaces: Close to 187A; distally, close to N79C.

Flower description:

- *Flower type and flowering habit*.—Single campanulate flowers arranged on axillary compound spikes; each spike with about 100 flowers; about 1,000 flowers develop per plant during the flowering season; flowers are mostly nodding to slightly outwardly-facing.
- *Fragrance*.—None detected.
- *Time of flowering*.—Plants flower continuously from the spring into the summer in The Netherlands; plants begin flowering about four months after planting.
- *Inflorescence longevity*.—Individual flowers last about a week on the plant; flowers not persistent.
- *Inflorescence length*.—About 30.1 cm.
- *Inflorescence width*.—About 10.4 cm.
- *Flower diameter*.—About 4.5 mm by 4.5 mm.
- *Flower depth (height)*.—About 9 mm.
- *Flower buds*.—Height: About 5 mm. Diameter: About 3 mm. Shape: Elliptic. Texture and luster: Densely pubescent; matte. Color: Distally, close to 63D and proximally, close to 58B.
- *Petals*.—Quantity and arrangement: Five petals in a single whorl. Length: About 4 mm. Width: About 1 mm. Shape: Oblanceolate. Apex: Acute. Base: Narrow attenuate. Margin: Entire to shallowly incised towards the apex. Texture and luster, upper surface: Smooth, glabrous; matte. Texture and luster, lower surface: Sparsely pubescent; matte. Color: When opening, upper and lower surfaces: Close to NN155D tinged with close to 186D; distally, close to N74D. Fully opened, upper and lower surfaces: Close to between 186D and NN155D; venation, close to between 186D and NN155D; color does not change with development.

*Sepals*.—Quantity and arrangement: Five sepals in a single whorl; lower 65% fused. Length: About 7 mm. Width: About 1.5 mm. Shape: Broadly ovate. Apex: Obtuse. Margin: Entire. Texture and luster, upper surface: Smooth, glabrous; matte. Texture and luster, lower surface: Densely pubescent; matte. Color: When opening, upper surface: Close to 186D; distally, close to 59D. When opening, lower surface: Close to 186D; distally, close to 59D; proximally, close to 63C. Fully opened, upper surface: Close to 59D. Fully opened, lower surface: Close to 59A.

*Peduncles*.—Length: About 62.2 cm. Diameter: About 2.5 mm. Strength: Moderately strong. Aspect: Erect to about 35° from vertical. Texture and luster: Densely pubescent; glossy. Color: Close to N186C.

*Pedicels*.—Length: About 3.5 mm. Diameter: About 0.5 mm. Strength: Moderately strong. Aspect: About 45° from peduncle axis. Texture and luster: Moderately to densely pubescent; slightly glossy. Color: Close to N186C.

*Reproductive organs*.—Androecium: Stamen number: Five per flower. Filament length: About 3 mm. Filament color: Close to 76D. Anther length: About 0.5 mm. Anther shape: Deltoid. Anther color: Close to 22B. Amount of pollen: Scarce. Pollen color: Close to 23A. Gynoecium: Pistil number: Two per flower. Pistil length: About 3.25 mm. Style length: About 3 mm. Style color: Close to 76D. Stigma diameter: About 0.2 mm. Stigma shape: Club-shaped. Stigma color: Close to 58A. Ovary color: Close to 76C.

*Seeds and fruits*.—To date, seed and fruit development have not been observed on plants of the new *Heuchera*.

Pathogen & pest resistance: To date, plants of the new *Heuchera* have not been observed to be resistant to pathogens and pests common to *Heuchera* plants.

Garden performance: Plants of the new *Heuchera* have been observed to have good garden performance and to tolerate high temperatures about 35° C. and to be suitable for USDA Hardiness Zones 3 through 9.

It is claimed:

1. A new and distinct *Heuchera* plant named 'IFHERB' as illustrated and described.

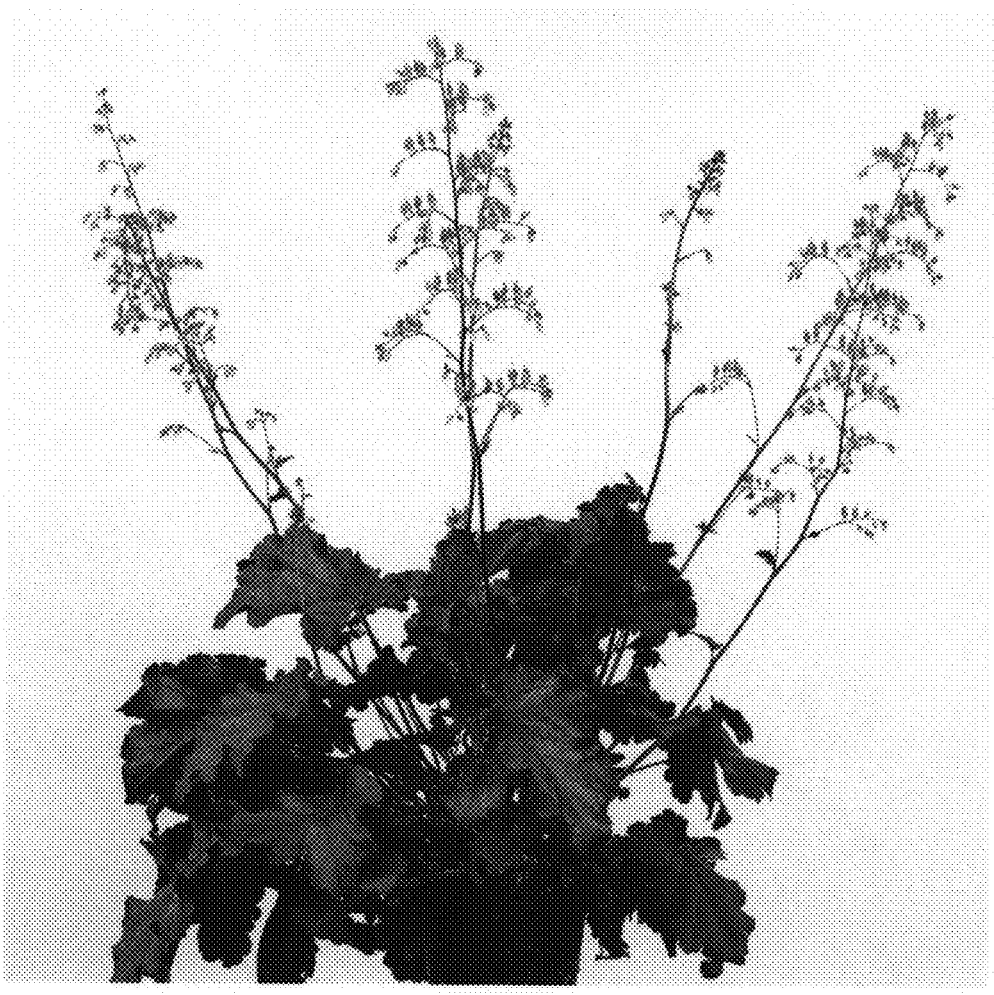

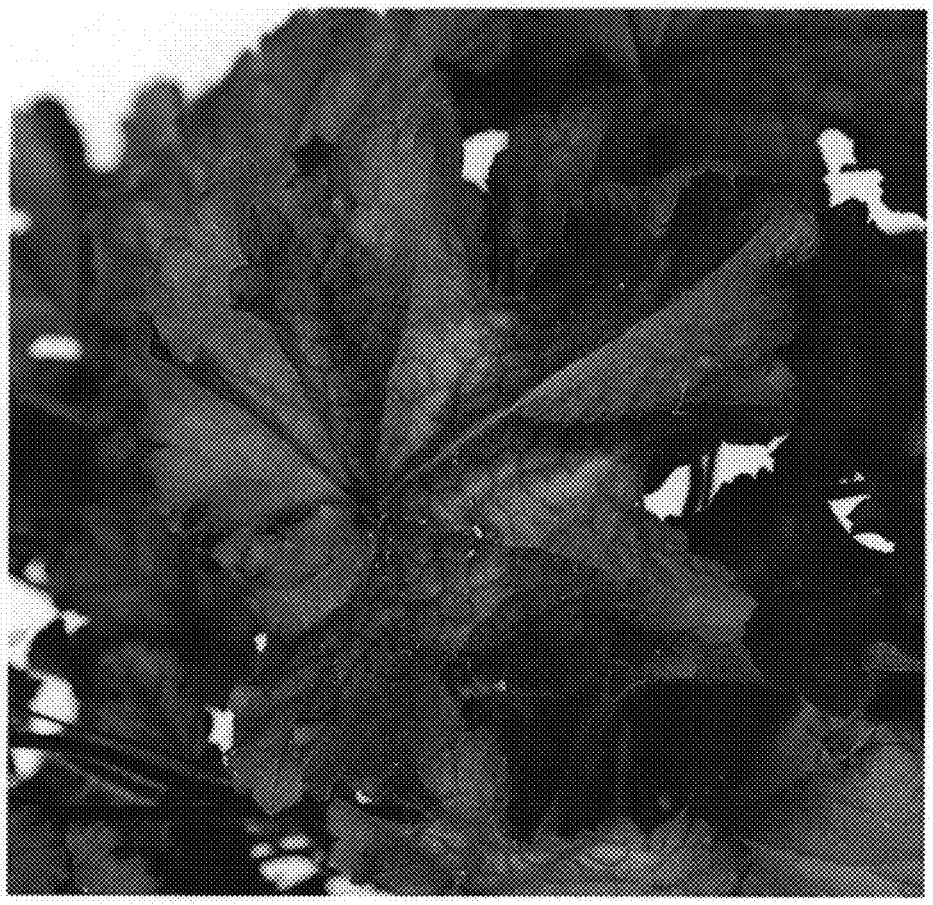
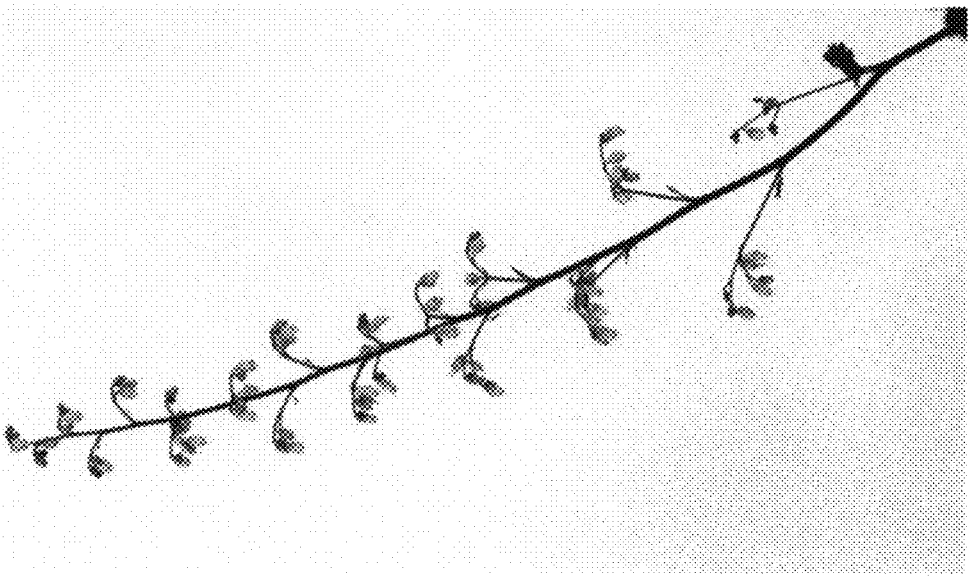

* * * * *